(12) United States Patent
Lu

(10) Patent No.: US 6,302,901 B1
(45) Date of Patent: Oct. 16, 2001

(54) APPARATUS FOR THERMAL LOW PERIODIC WAVE TREATMENT

(76) Inventor: Yi-Jen Lu, P.O. Box 82-144, Taipei (TW)

( * ) Notice: Subject to any disclaimer, the term of this patent is extended or adjusted under 35 U.S.C. 154(b) by 0 days.

(21) Appl. No.: 09/472,791

(22) Filed: Dec. 28, 1999

(51) Int. Cl.$^7$ ........................................................ A61F 7/00
(52) U.S. Cl. .............................................. 607/96; 607/100
(58) Field of Search ............................... 607/96, 59, 100, 607/1, 104, 102; 128/898; 600/411

(56) References Cited

U.S. PATENT DOCUMENTS

| | | | |
|---|---|---|---|
| 5,601,618 | * | 2/1997 | James ...................................... 607/71 |
| 6,021,348 | * | 1/2000 | James ........................................ 607/3 |
| 6,066,164 | * | 5/2000 | Macher et al. .......................... 607/96 |

* cited by examiner

Primary Examiner—Michael Peffley
Assistant Examiner—P. J. Vrettakos
(74) Attorney, Agent, or Firm—A & J

(57) ABSTRACT

An apparatus for thermal low periodic wave treatment includes a pair of shock plates, a storage battery and a main control circuit, and a housing enclosing the main control circuit and the storage battery. The apparatus is characterized in that the shock plates are each provided with a sensing plate and a plurality of heating wires, and by way of a transmission wire, the shock plates are linked to the main control circuit, and any corresponding action of the main control circuit is transmitted to the shock plates and at the same time, provides the shock plates with a heat source and low periodic wave pulse source. The main control circuit includes a single chip CPU, and a DC charger switching circuit directly connected thereto, a voltage-stabilizing circuit, a ringing circuit, a heating circuit, a press key control circuit, a voltage-elevating and feedback monitoring circuit, a polar switching circuit and a display.

1 Claim, 2 Drawing Sheets

US 6,302,901 B1

APPARATUS FOR THERMAL LOW PERIODIC WAVE TREATMENT

BACKGROUND OF THE INVENTION a) Technical Field of the Invention

The present invention relates to an apparatus for thermal heat low periodic wave treatment, and in particular, a CPU is used to control the operation of various circuits such that the electrode plates of the apparatus output heat source and low periodic wave pulse source, and the part of the body contacting the electrode plates is appropriately thermal treated or electrically stimulated in the process of treatment.

b) Description of the Prior Art

In contemporary society of today, people working long hour in office for an extended are frequently found to have sickness such as muscle pain, stiff-neck, etc. This is probably due to the fact that too much working pressure on these people and less exercise has caused these sicknesses to the muscles. Accordingly, it is essential that the body needs treatment so that the muscle, and the bones of the body are at a relaxation state.

SUMMARY OF THE INVENTION

Accordingly, it is an object of the present invention to provide an apparatus for thermal heat low periodic wave treatment, wherein the heat source and the pulse source can simultaneously be transmitted to the parts of the body which are in contact, and the parts of the body are thermally treated and also treated with low periodic wave electrically shock.

Another object of the present invention is to provide an apparatus for thermal heat low periodic wave treatment, wherein a multiple-stages temperature and a shock strength control can be selected for individual person of different adaptability.

Yet another object of the present invention is to provide an apparatus for thermal heat low periodic wave treatment, wherein the thermal shock stimulates the muscles to cause a smooth blood circulation in the body which heals muscle cramps, and other muscles sickness, etc.

Yet another object of the present invention is to provide an apparatus for thermal heat low periodic wave treatment, wherein the rate of metabolism of the body can be increased via treatment with the apparatus. One aspect of the present invention is to provide an apparatus for thermal heat low periodic wave treatment comprising a pair of shock plates, a storage battery and a main control circuit, and a housing enclosing the main control circuit and the storage battery, characterized in that the shock plates are each provided with a sensing plate and a plurality of heating wires, by means of a transmission wire, the shock plates are linked to the main control circuit, any corresponding action of the main control circuit is transmitted to the shock plates and at the same time, provides the shock plates with heat source and low periodic wave pulse source; the main control circuit includes a single chip CPU, and a DC charger switching circuit directly connected thereto, a voltage-stabilizing circuit, a ringing circuit, a heating circuit, a press key control circuit, a voltage-elevating and feedback monitoring circuit, a polar switching circuit and a display, wherein the DC charger switching circuit provides as a power source for DC battery or AC power source; the voltage-stabilizing circuit provides a fixed voltage elevation for the feedback monitoring circuit; the ringing circuit provides an indication alarm for various operation status; the heating circuit provides a heat source as a result of impedance action of the heating wires if current passes to the transmission wires, wherein, a power control of the apparatus employs Pulse Width Modulation for controlling heating efficiency, the press key control circuit is the operation link of the external control keys mounted at the housing, the control signals of the control keys are transmitted to the CPU and the individual circuit to provide corresponding actions; the monitoring circuit is used to receive stabilized voltage provided by the voltage-stabilizing circuit to elevate the output strength of the low periodic wave, after the high voltage capacitor of the monitoring circuit releases current, and output via the PWM control line and via the transmission wires to the sensing plate of the shock plates; the polar switching circuit is in combination with the monitoring circuit, wherein via full bridge switch and the human body, a feedback circuit is formed, if the electrode dislocates from the body the feedback circuit cannot be formed; and a display to output the status of the treating device.

The foregoing and other objects, features, aspects and advantages of the present invention will become more apparent from the following detailed description of the present invention when taken in conjunction with the accompanying drawings.

DETAILED DESCRIPTION OF THE PREFERRED EMBODIMENT

Figure 1:
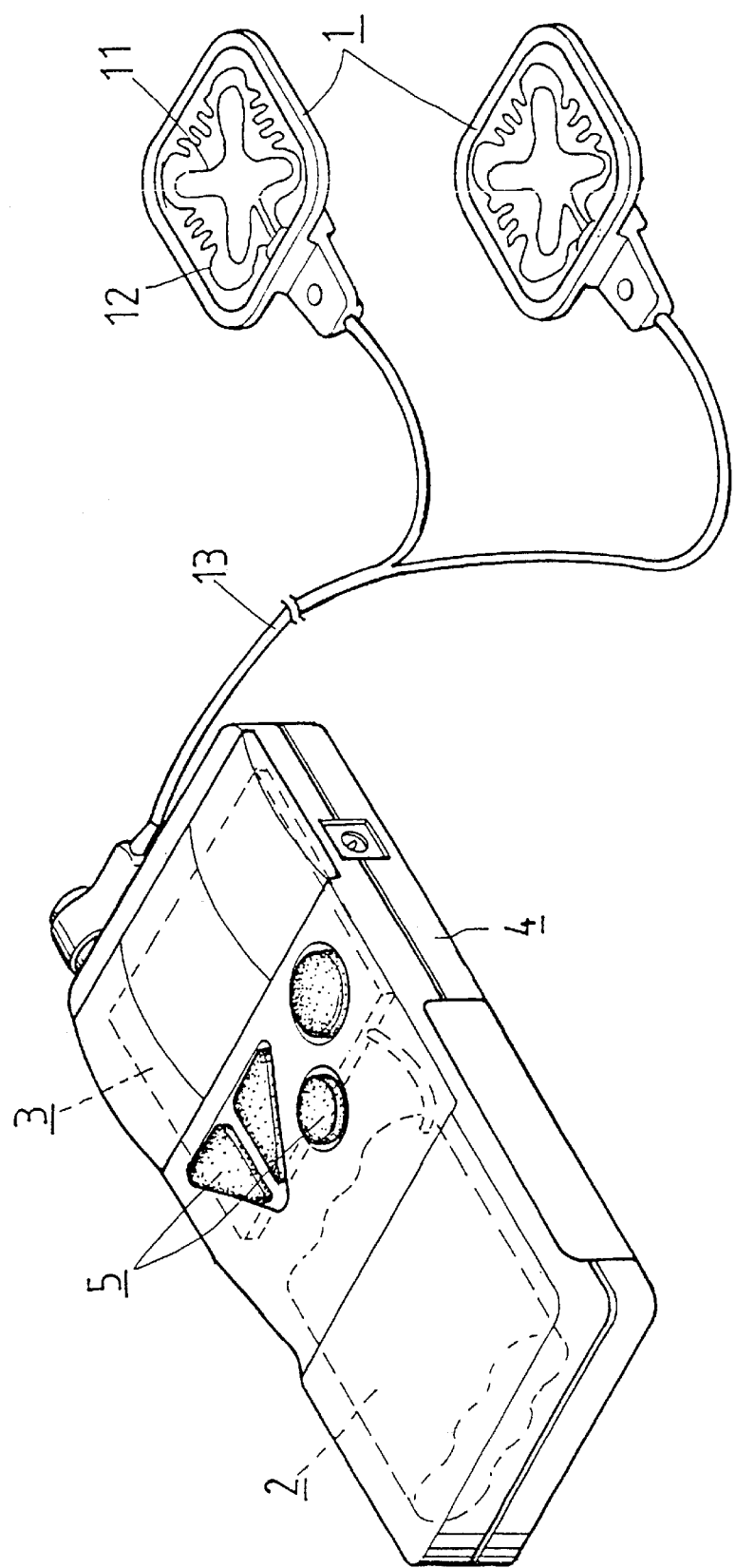
FIG. 1 is a perspective view of an apparatus for thermal heat low periodic wave treatment in accordance with the present invention.
Figure 2:
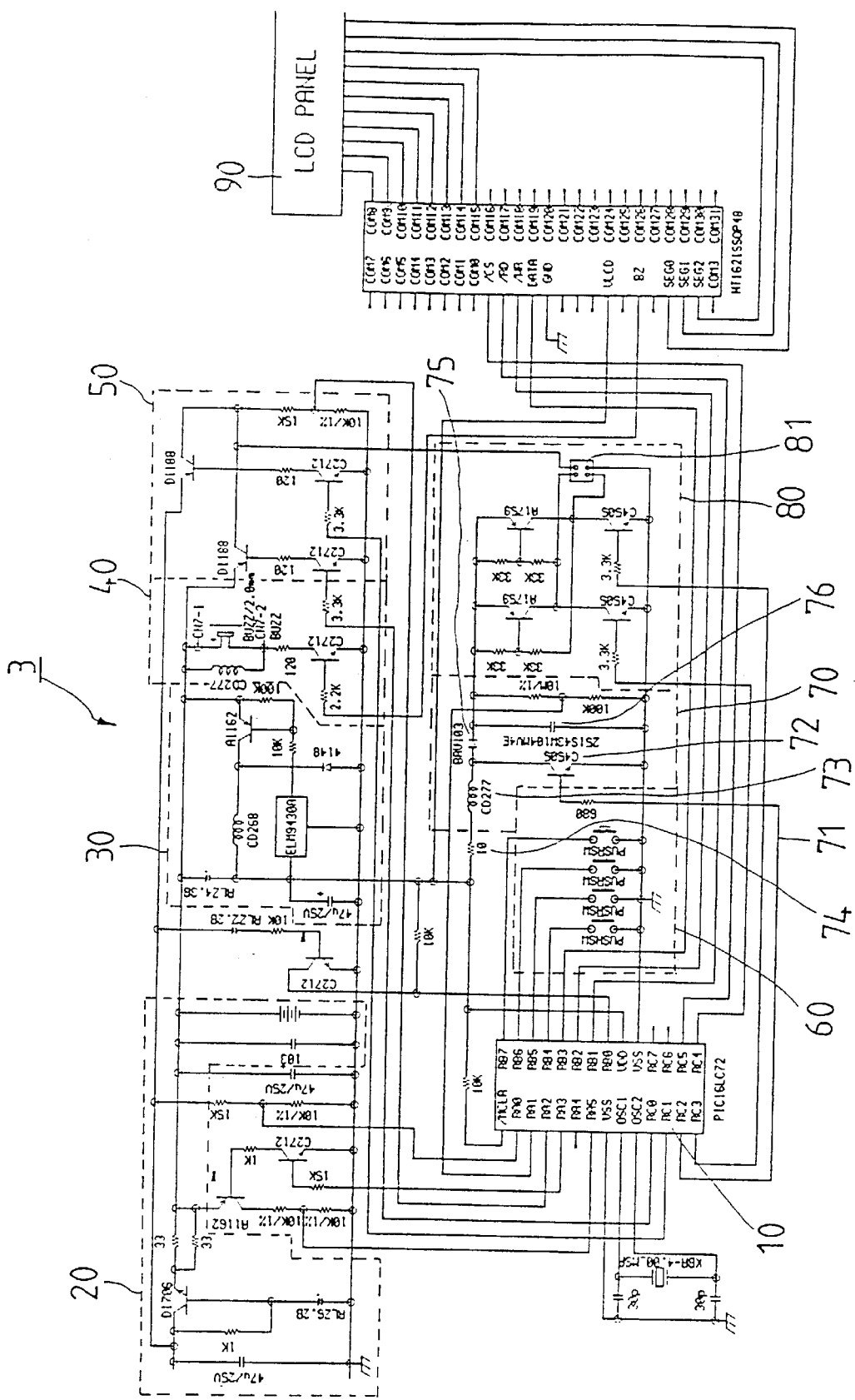
FIG. 2 is the circuit layout of the main control circuit in accordance with the present invention.

Referring to FIGS. 1. and 2, an apparatus for thermal heat low periodic treatment of the present invention comprises a pair of shock plates 1, a storage battery 2 and a main control circuit 3, wherein the main circuit 3 and the storage battery 2 are located within a housing 4 having a plurality of control keys 5. A sensing plate 11 and a plurality of heating wires 12 are provided on the shock plates 1, and are connected to the main control circuit 3 by a transmission wire 13. The corresponding action of the main control circuit 3 is transmitted to the shock plates 1. The main control circuit 3 includes a single chip CPU 10, a DC charger switching circuit 20 linked to the CPU 10, a voltage stabilizing circuit 30, a ringing circuit 40, a heating circuit 50, a press key control circuit 60, a voltage elevating and feedback monitoring circuit 70, a polar switching circuit 80 and a display 90.

In accordance with the present invention, the switching circuit 20 allows the apparatus to use either DC or AC as the power source. The voltage-stabilizing circuit 30 provides a stable voltage for the monitoring circuit 70. The ringing circuit 40 is used to provide warming alarms for various functions of the present apparatus. The heating circuit 50 provides a heat source as a result of impedance action of the heating wires 12 when current passes to the transmission wires 13. In order to control the rate of heating, the electrical power control and the low periodic wave-strength control are similarly employing a Pulse-Width-Modulation (PWM). The potential of the electric power output end is feedback by partial voltage of resistance via the operation of the CPU 10 to obtain the pulse width value to drive the electrical power transistor. The control circuit 60 is the operation link of the external control key 5 at the housing 4. The control signal of the control key 5 is transmitted to CPU 10 to provide corresponding actions of the individual circuits. The monitoring circuit 70 is used to receive the stabilized voltage provided by the voltage-stabilizing circuit 30. It has two functions. Firstly, it is used to elevate the output strength of the low periodic wave. When the PWM control wire 71 outputs a high potential, the transistor switch 72 is at the state of electrically conduction. The stabilized voltage source provided by the voltage-stabilizing circuit 30 forms a feedback circuit via a current-limiting resistance 74, an electric sensor 73 and a transistor switch 72. The electric sensor 73 is an element stored charged energy. When the output of PWM control wire 71 changes from high potential to low potential, the transistor switch 72 becomes open and the stored energy at the electric sensor 73 changes the high voltage capacitor 76 via a diode 75 to attain a voltage elevation. By using PWM control wire 71 as a driving means, the elevation circuit can improve the drawbacks produced by using a transistor switch or by the method of manually adjusting the partial voltage of the variable resistance. In accordance with the present invention, the multiplication of the fixed current and the rate of working period are used as the current-releasing control of different voltage strength. In this case, the impedance exhaustion of the individual element is not required. Thus, the electrical power efficiency can be increased (by 90% above). The method of working is by setting the software parameters of the CPU 10 to produce a periodic control signal. The modulated working periodic signal is output via the CPU 10 to control the stored electrical charges at the high voltage capacitor 76 of the monitoring circuit 70. The stored electrical charges of the high voltage capacitor 76 are the basis for the output voltage strength of the low periodic wave.

Another function of the monitoring circuit 70 is that it is used to prevent the output of an inappropriate voltage. When the shock plates 1 are dislocated, the output voltage switch is automatically closed. This is done so by using the high voltage capacitor 76 of the monitoring circuit 70 via a fully opened bridge switch of the switching circuit 80 and the human body to form a feedback. As a result of the fully opened bridge switch to cause the high voltage capacitor to produce a current, if the shock plates 1 are dislocated from the body; a feedback circuit is not formed. Thus, the high voltage capacitor 76 will not release current. Thus, the voltage drop at the end terminal of the high voltage capacitor 76 can determine whether the output voltage pulse has protected the user. The strength setting is provided with a reset function so as to prevent accidental electrical shock. The current release monitoring and detecting of the capacitor is done by, after a partial voltage of the resistance, input the analog/digital conversion to obtain a digital amount corresponding to that at the end terminal of the high voltage capacitor 76. This digital amount is transmitted to CPU 10 as a basic for operation. The initiation of the protection programs and the setting of the reset strength are determined by the comparison of the voltage drop at the end terminal of the high voltage capacitor before and after the full-bridge switching action. The above operation employs CPU 10 as the operation control.

In accordance with the present invention, the display 90 can provide the operation status and output status of the present apparatus for the convenient operation of the user. The action and interrelationship of the various circuits and the display are control by the CPU 10. The monitoring circuit 70 and heating circuit 50 employ Pulse-Width-Modulator (PWM) as an output means for modulation strength and electrical power strength to effectively increase the electrical power efficiency and to decrease power loss.

By means of the CPU 10 and the individual circuits, the shock plates 1 can simultaneously output the heat source and the low periodic wave pulse source. The heat source and the pulse source can be controlled in a multiple stage output method, so as to provide appropriate heat treatment and low periodic wave pulse electrical shock stimulation to various parts of the body.

In accordance with the present invention, in operation, the shock plates 1 are adhered to the parts of the body which are to be treated. By controlling the various control keys 5 on the housing 4, the CPU 10 and various interconnected circuits are driven to operate. The temperature and the strength of the low periodic wave pulse can be selected (in multiple stages) via PWM control. The heat source and the pulse source can be simultaneously transmitted to the contacted parts of the body by the heating wire 12 of the shock plates 1 and the sensing plate 11.

In accordance with the present invention, there are advantages provided by the present treatment apparatus as follows:

(a) As a single chip CPU is employed to control the entire actions and the interrelation actions, the speed of control is fast and the control is accurate. In addition, the power consumption is low as PWM is employed to control the low periodic wave and heat source output.

(b) The present apparatus provides dual functions, heat treatment and low periodic wave, which provides thermal treatment and electrically shock treatment. In addition, the temperature and the strength of the electrical shock can be adjusted in multiple stages.

(c) The present apparatus is provided with a feedback monitoring function and a pulse output strength reset function. These functions can protect the user from accidentally shock.

While the invention has been described with respect to a preferred embodiment, it will be clear to those skilled in the art that modifications and improvements may be made to the invention without departing from the spirit and scope of the invention. Therefore, the invention is not to be limited by the specific illustrative embodiment, but only by the scope of the appended claims.

I claim:

1. An apparatus for thermal heat low periodic wave treatment comprising a pair of shock plates, a storage battery and a main control circuit, and a housing enclosing the main control circuit and the storage battery, characterized in that the shock plates are each provided with a sensing plate and a plurality of heating wires, by means of a transmission wire, the shock plates are linked to the main control circuit, any corresponding action of the main control circuit is transmitted to the shock plates and at the same time, provides the shock plates with heat source and low periodic wave pulse source; the main control circuit includes a single chip CPU, and a DC charger switching circuit directly connected thereto, a voltage-stabilizing circuit, a ringing circuit, a heating circuit, a press key control circuit, a voltage-elevating and feedback monitoring circuit, a polar switching circuit and a display, wherein the DC charger switching circuit provides as a power source for DC battery or AC power source; the voltage-stabilizing circuit provides a fixed voltage elevation for the feedback monitoring circuit; the ringing circuit provides an indication alarm for various operation status; the heating circuit provides a heat source as a result of impedance action of the heating wires if current passes to the transmission wires, wherein, a power control of the apparatus employs Pulse Width Modulation for controlling heating efficiency, the press key control circuit is the operation link of the external control keys mounted at the housing, the control signals of the control keys are transmitted to the CPU and the individual circuit to provide corresponding actions; the monitoring circuit is used to receive stabilized voltage provided by the voltage-stabilizing circuit to elevate the output strength of the low periodic wave, after the high voltage capacitor of the monitoring circuit releases current, and output via the PWM control line and via the transmission wires to the sensing plate of the shock plates; the polar switching circuit is in combination with the monitoring circuit, wherein via full bridge switch and the human body, a feedback circuit is formed, if the electrode dislocates from the body the feedback circuit cannot be formed; and a display to output the status of the treating device.

* * * * *